(12) United States Patent
Lever et al.

(10) Patent No.: US 6,500,964 B2
(45) Date of Patent: Dec. 31, 2002

(54) METHOD OF PRODUCING HIGH YIELD ALDITOL ACETALS WITH MINERAL ACIDS AND SURFACTANTS

(75) Inventors: John G. Lever, Spartanburg, SC (US); Darin L. Dotson, Spartanburg, SC (US); John D. Anderson, Moore, SC (US); Jeffrey R. Jones, Inman, SC (US); Shawn R. Sheppard, Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 11 days.

(21) Appl. No.: 09/815,487

(22) Filed: Mar. 23, 2001

(65) Prior Publication Data

US 2002/0137953 A1 Sep. 26, 2002

(51) Int. Cl.$^7$ .............................................. C07D 323/14
(52) U.S. Cl. ...................................... 549/364; 549/363
(58) Field of Search ......................................... 549/364

(56) References Cited

U.S. PATENT DOCUMENTS

| | | | |
|---|---|---|---|
| 4,267,110 A | 5/1981 | Uchiyama | 260/340.7 |
| 4,562,265 A | 12/1985 | Machell | 549/364 |
| 4,902,807 A | 2/1990 | Kobayashi et al. | 549/364 |
| 5,023,354 A | 6/1991 | Salome et al. | 549/364 |
| 5,241,080 A | 8/1993 | Kobayashi et al. | 549/201 |
| 5,731,474 A | 3/1998 | Scrivens et al. | 568/592 |

*Primary Examiner*—Alan L. Rotman
*Assistant Examiner*—Raymond Covington
(74) *Attorney, Agent, or Firm*—Terry T. Moyer; William S. Parks

(57) ABSTRACT

This invention relates to a process for preparing alditol acetals, such as dibenzylidene sorbitols, monobenzylidene sorbitols, and the like, through the reaction of unsubstituted or substituted benzaldehydes with alditols (such as sorbitol, xylitol, and ribitol) in the presence of a mineral acid and at least one surfactant having at least one pendant group of 6 carbon chains in length. Such a reaction provides a cost-effective, relatively safe procedure that provides excellent high yields of alditol acetal product. Furthermore, such a specific reaction is also the best known procedure for the production of certain compounds which can be easily separated from other formed isomers. Additionally, such a procedure facilitates the production of certain asymmetric alditol acetal compounds and compositions in acceptable yields as well. Such alditol acetals are useful as nucleating and clarifying agents for polyolefin formulations and articles, as one example.

24 Claims, No Drawings

METHOD OF PRODUCING HIGH YIELD ALDITOL ACETALS WITH MINERAL ACIDS AND SURFACTANTS

FIELD OF THE INVENTION

This invention relates to a process for preparing alditol acetals, such as dibenzylidene sorbitols, monobenzylidene sorbitols, and the like, through the reaction of unsubstituted or substituted benzaldehydes with alditols (such as sorbitol, xylitol, and ribitol) in the presence of a mineral acid and at least one surfactant having at least one pendant group of 6 carbon chains in length. Such a reaction provides a cost-effective, relatively safe procedure that provides excellent high yields of alditol acetal products, particularly those which have heretofore not been readily available due to processing limitations, such products including bis(5-indanylidene)sorbitol. Furthermore, such a specific reaction is also the best known procedure for the production of certain compounds which can be easily separated from other formed isomers. Additionally, such a procedure facilitates the production of certain asymmetric alditol acetal compounds and compositions in acceptable yields as well. Such alditol acetals are useful as nucleating and clarifying agents for polyolefin formulations and articles, as one example.

BACKGROUND OF THE PRIOR ART

All U.S. Patent documents and other publication discussed below are herein entirely incorporated by reference.

Dibenzylidene sorbitol ("DBS"), substituted DBS's, such as can be made with alkyl substituted aromatic aldehydes, and related acetals have found utility as nucleating agents, clarifying agents, gelling agents, processing aids, and strength modifiers in polyolefin resins, polyester resins, deodorant, and antiperspirant compositions; hydrocarbon fuels; waste liquids, especially those containing organic impurities; and paint.

Alditol acetals, such as DBS derivative compounds, are typically prepared by the condensation reaction of an aromatic aldehyde with a polyhydric alcohol, for example, without limitation, sorbitol, xylitol, ribitol, and the like. For DBS structures, such reactions involve two moles of the aldehyde and one mole of the alcohol. Examples of suitable processes may be found in Uchiyama, U.S. Pat. No. 4,267,110, Murai et al., U.S. Pat. No. 3,721,682; Murai et al., U.S. Pat. No. 4,429,140; Machell, U.S. Pat. No. 4,562,265; Kobayashi et al., U.S. Pat. No. 4,902,807; Salome et al., U.S. Pat. No. 5,023,354; and Scrivens et al., U.S. Pat. No. 5,731,474.

Unfortunately, these previous reaction procedures all suffer significant drawbacks for utilization within a greater breadth of reactions. The first procedure taught was by Uchiyarna solely for the production of limited DBS compounds of the unsubstituted benzaldehyde type. The lack of versatility of such a procedure has severely limited its implementation within different DBS compound producing methods. Solvent-based systems have been developed for higher yield and greater versatility of DBS formation, for instance, within the Murai et al., Scrivens et al, and Kobayashi et al. patents, which all concerned reactions for the production of un-, mono-, or di-substituted dibenzylidene sorbitols. Although these reactions are highly effective in producing high yield, high purity DBS compounds, the solvents needed are expensive and the energy required to effectuate necessary mixing and high temperatures is also expensive. In an effort to reduce such solvent costs, low temperature low temperature aqueous procedures have been developed, such as in the Machell and Salome et al. patents. Machell requires the utilization of a mineral acid as the catalyst alone for acetalization; Salome et al. specifically exclude any mineral acids from their procedure and instead rely solely upon the presence of relatively large amounts of arylsulfonic acid catalysts to effectuate acetalization of the benzaldehyde and alditol components. Machell thus requires large amounts of mineral acids whereas Salome et al. require expensive arylsulfonic compounds (such as para-toluenesulfonic acid, naphththalene sulfonic acid, and the like). More importantly, however, it has now been found that there are key problems with both types of procedures which require improvement. For instance, the previous uses of acid alone, as in Machell, or with arylsulfonic acids alone, as in Salome et al., as acetalization catalysts have proven very difficult for a number of reasons. The Machell method of acid alone has suffered from a lack of effectiveness in producing highly-substituted DBS derivatives, apparently, and without intending to be limited to any specific scientific theory, from the lack of contacting a sufficient amount of catalyst with the reactants themselves to permit combination and thus acetalization. In the past, such mineral acids have proven to be excellent catalysts alone for un- or certain minimally-substituted benzaldehydes (e.g., p-methylbenzaldehyde). Apparently, di-substituted benzaldehydes and above are more hydrophobic and thus do not solubilize well within aqueous acid formulations. In such a situation, the catalysis of di-substituted (or higher) benzaldehydes with alditol is nearly nonexistent due to a lack of effective contact between all three components (e.g., acid, benzaldehyde, and alditol). Benzaldehyde and p-methylbenzaldehyde, on the other hand, are much more soluble within such an aqueous acid formulation and thus more easily contact the acid catalyst, thereby permitting a more effective acetalization of the alditol for very high yields. Thus, from a versatility standpoint, the use of mineral acids alone, although the best catalyst for acetalization procedures, does not effectively contact with certain reactants due to solubility considerations. The Salome et al. method requires a very large amount of very expensive arylsulfonic compounds (Salome et al. require a molar ratio of benzaldehyde to arylsulfonic acid of at least 1:0.6) as catalysts alone within the reaction mixture. Although such large amounts of arylsulfonic acid catalyst have proven to be effective for certain reactions of benzaldehydes with alditols, a combination of both costs and lack of versatility has been problematic from a large-scale industrial production standpoint. The arylsulfonic acids alone either do not contact sufficiently (as with p-toluenesulfonic acid) or are not strong enough acid catalysts alone to provide the needed reactivity for greater versatility with different benzaldehyde reactants at lower levels at concentration within the reaction mixture. Thus, the cost of such arylsulfonic acids, being relatively high and extremely high in comparison with the more effective mineral acids, pose considerable economic problems for the user.

Clearly, the utilization of less expensive mineral acids, which are better catalysts at lower amounts, is a preferred method from a cost perspective; however, the lack of versatility has been a hindrance to widespread use and effectiveness of such a method. The yield offered by both teachings is acceptable, however the versatility of producing large variations of different DBS compounds is questionable. There has been a need to provide a procedure which permits production of not only standard p-methyldibenzylidene sorbitol (MDBS), 3,4- dimethyldibenzylidene sorbitol (DMDBS), and dibenzylidene sorbitol (DBS), but other compounds which heretofore have been impossible to produce either at all or at least in any acceptable yield and/or purity. As a few examples, 1,3:2,4-bis(5-indanylidene)sorbitol has been unavailable as a product due to the lack of production of such a compound in any yield acceptable on an industrial scale or without the need for using excess amounts of the reactive benzaldehyde. Such a compound is known to provide excellent clarifying and nucleating benefits within polypropylene formulations, but, again, has not been readily utilized in such a market because of the lack of effective production methods for large-scale reliable availability. Also, other types of compounds, such as certain symmetrical compounds [e.g., 1,3:2,4-bis(3-ethyl-4-methylbenzylidene) sorbitol and 1,3:2,4-bis(3,4-diethylbenzylidene) sorbitol] have not been available as pure product due to the presence of isomers and/or reaction mixture additives which could not be readily removed or separated from the desired compounds. With the lack of versatility, cost problems, potential corrosiveness, or all three, the above-listed and discussed methods have proven ineffective in providing needed advances in DBS production technology. Without any further teachings or fair suggestions, expansions into other DBS compound areas to develop alternative and more specialized polyolefin nucleation and/or clarification markets and products has been hampered. Hence, there is a need to develop a procedure to facilitate high yield, reliable, versatile, cost-effective, and safe production of both standard and novel alditol acetal derivative compounds. To date, again, although some processes do exist permitting production of limited types of DBS compounds, or provide some versatility, but at a rather large cost economically, there simply is no effective alternative to expand the production capabilities of a wide array of such alditol acetal derivatives.

OBJECTS OF THE INVENTION

Therefore, an object of the invention is to provide a process a highly versatile process for producing high yields of alditol acetal derivative compounds, most notably, without limitation symmetrical and asymmetrical DBS compounds. A further object of the invention is to provide a highly effective manner of producing such compounds which heretofore could not be produced in high yields without incurring potential problems from cost and/or safety perspectives, particularly in a large-scale procedure. Another object of the invention is to provide a method which also permits the production of monoacetal derivatives and asymmetrical dibenzylidene compounds. Additionally, it is an object of this invention to provide a method of producing alditol acetal derivative compounds which permits the utilization of any type of surfactant component thereby facilitating utilization of such a procedure on a widespread basis and permitting the user greater versatility and fewer limitations on reaction component selections.

DETAILED DESCRIPTION OF THE INVENTION

Accordingly, this invention encompasses a method of producing an alditol acetal derivative compound comprising the reaction of at least one aromatic benzaldehyde and at least one alditol in the presence of water, at least one mineral acid, and at least one surfactant. Furthermore, this invention encompasses a method of producing an alditol acetal derivative compound comprising the reaction of at least one-half mole of at least one aromatic benzaldehyde and at least one mole of an alditol in the presence of water, at least one mineral acid, and at most 0.01 mole (in relation to the amount of benzaldehyde present) of a surfactant. The actual reaction mixtures for these methods are also encompassed within this invention as well.

It has now been found that the addition of small molar amounts of long-chain surfactant to the reaction mixture permits a more effective yield of acetal alditol derivatives result through mineral acid catalysis of benzaldehyde and alditol components. Furthermore, such an inventive procedure permits tailoring of solubilities, and potential reduction of mineral acid amounts and/or concentrations to permit a more environmental, safe reaction as well.

Any alditol acetal derivative compound may be produced by the inventive method, including, as preferred but not as the limited type of alditol acetal compound, DBS compounds. Specific DBS derivatives produced by this inventive method include, as merely examples: 1,3:2,4-dibenzylidene sorbitol; 1,3:2,4-bis(p-methylbenzylidene)sorbitol; 1,3:2,4-bis(p-chlorobenzylidene)sorbitol; 1,3:2,4-bis(2,4-dimethyldibenzylidene)sorbitol; 1,3:2,4-bis(p-ethylbenzylidene)sorbitol, abbreviated as EDBS; 1,3:2,4-bis(3,4-dimethyldibenzylidene)sorbitol, abbreviated as 3,4-DMDBS; 1,3:2,4-bis(3,4-diethylbenzylidene)sorbitol; 1,3;2, 4-bis(3-ethyl4-methylbenzylidene)sorbitol; 1,3:2,4-bis(4-chloro-3-methylbenzylidene)sorbitol, 1,3:2,4-bis(3-chloro-4-methylbenzylidene)sorbitol, 1,3:2,4-bis(3-bromo-4-isopropylbenzylidene)sorbitol, 1,3:2,4-bis(3-bromo-4-methylbenzylidene)sorbitol, and 1,3:2,4-bis(3-bromo-4-ethylbenzylidene)sorbitol. Other compounds include monoacetal derivatives, such as, without limitation 2,4-mono(3,4-dimethylbenzylidene)sorbitol, 2,4-mono(4-fluoro-3-methylbenzylidene)sorbitol, and the like (e.g., instead of two moles of aromatic aldehyde, only one is reacted with the alditol) and tri-acetals (e.g., three moles of aromatic aldedhyde to one of alditol). Furthermore, asymmetrical compounds may be produced, such as, without limitation: 1,3-O-(3,4-dichlorobenzylidene):2,4-O-(3,4-dimethylbenzylidene)sorbitol, 1,3-O-(3,4-difluorobenzylidene):2,4-O-(3,4-dimethylbenzylidene) sorbitol, 1,3-O-(3,4-dichlorobenzylidene):2,4-O-(3,4-dimethoxybenzylidene)sorbitol, 1,3-O-(3,4-dichlorobenzylidene):2,4-O-(5-indanylidene)sorbitol, 1,3-O-(4-nitrobenzylidene):2,4-O-(3,4dimethylbenzylidene) sorbitol, and 1,3-O-(4-nitrobenzylidene):2,4-O-(3,4-methylenedioxybenzylidene)sorbitol, 1,3-O-(4-fluoro-3-methylbenzylidene):2,4-O-(3,4-dimethylbenzylidene) sorbitol, 1,3-O-(3,4-dimethylbenzylidene):2,4-O-(4-fluoro-3-methylbenzylidene)sorbitol, 1,3-O-(4-fluoro-3-methylbenzylidene):2,4-O-(3-fluoro-4-methylbenzylidene) sorbitol, 1,3-O-(3-fluoro-4-methylbenzylidene):2,4-O-(4-fluoro-3-methylbenzylidene)sorbitol, 1,3-O-(4-fluoro-3-methylbenzylidene):2,4-O-(4-chlorobenzylidene)sorbitol, 1,3-O-(4-chlorobenzylidene):2,4-O-(4-fluoro-3-methylbenzylidene)sorbitol, 1,3-O-(4-chloro-3-methylbenzylidene):2,4-O-(3-chloro-4-methylbenzylidene) sorbitol, 1,3-O-(3-chloro-4-methylbenzylidene):2,4-O-(4-chloro-3-methylbenzylidene)sorbitol, 1,3-O-(4-fluoro-3-methylbenzylidene):2,4-O-(5',6',7',8tetrahydro-2-napthylidene)sorbitol, 1,3-O-(5',6',7',8'-tetrahydronapthylidene):2,4-O-fluoro-3-methylbenzylidene)sorbitol, 1,3-O-(4-Chloro-3-methylbenzylidene)-2,4-O-(5',6', 7',8'-tetrahydro-2-napthylidene)sorbitol, 1,3-O-(5',6',7',8'-tetrahydronapthylidene):2,4-O-(4-chloro-3-methylbenzylidene)sorbitol, 1,3-O-(3-bromo-4-ethylbenzylidene):2,4-O-(3,4-dimethylbenzylidene)

sorbitol, 1,3-O-(3-bromo-4-isopropylbenzylidene):2,4-O-(3,4-dimethylbenzylidene)sorbitol, 1,3-O-(3-bromo-4-methylbenzylidene):2,4-O-(3,4-dimnethylbenzylidene) sorbitol, 1,3-O-(4-chlorobenzylidene):2,4-O-(3-bromo-4-isopropylbenzylidene)sorbitol, 1,3-O-(4-t-butylbenzylidene):2,4-O-(3,4-dimethylbenzylidene) sorbitol, 1,3-O-(3,4-dimethylbenzylidene):2,4-O-(t-butylbenzylidene)sorbitol, 1,3-O-(3,4-dimethoxybenzylidene):2,4-O-(3,4-dimethylbenzylidene) sorbitol, 1,3-O-(3,4-dimethylbenzylidene):2,4-O-(3,4-dimethoxybenzylidene)sorbitol, 1,3-O-(3,4-methylenedioxybenzylidene):2,4-O-(3,4-dimethylbenzylidene)sorbitol, 1,3-O-(3,4-dimethylbenzylidene):2,4-O-(3,4-methylenedioxybenzylidene)sorbitol, 1,3-O-(4-isopropylbenzylidene):2,4-O-(3,4-dimethylbenzylidene) sorbitol, 1,3-O-(3,4-dimethylbenzylidene):2,4-O-(4-isopropylbenzylidene)sorbitol, 1,3-O-(3,4-dimethylbeznylidene):2,4-O-(2-naphthylbenzylidene) sorbitol, and 1,3-O-(2-naphthylbenzylidene):2,4-O-(3,4-dimethylbenzylidene)sorbitol.

Such a diacetal compound, as well as any type of DBS system, may be produced through the condensation reaction between two moles of an aromatic aldehyde and one mole of a polyhydric alcohol. The aldehyde and polyhydric alcohol are generally provided in the reaction mixture in a ratio from 1:1 to 4:1, preferably 1.5:1 to 2.5:1, respectively. The aromatic aldehydes are single or fused double ring aldehydes having at least one unsaturated hydrocarbon ring, and include benzaldehyde, naphthaldehyde, 5-formylindan and 6-formyltetralin. The aromatic aldehydes may be unsubstituted or have from one to five substituent groups selected from $C_{1-6}$ alkyl, $C_{1-6}$ alkoxy, hydroxy, halogen, $C_{1-6}$ alkylthio, $C_{1-6}$ alkylsulfoxy, $C_{3-5}$ alkylene forming a carbocyclic ring with adjacent carbon atoms on an unsaturated hydrocarbon ring, carboxyl, ($C_1$–$C_{20}$ alkyloxy)carbonyl, ($C_1$–$C_{20}$ alkyloxy)ethyloxycarbonyl, ($C_1$–$C_{12}$ alkyl)phenyl, halogenated phenyl, ($C_1$–$C_{12}$ alkoxy)phenyl, ($C_1$–$C_{12}$ alkyloxy)ethyloxyethyloxycarbonyl and ($C_1$–$C_{12}$ alkyloxy) ethyloxy-ethyloxyethyloxycarbonyl groups, methylenedioxy (e.g., piperonal), or any of the benzylidene groups may be polyphenyl (such as naphthyl). Preferably, the aromatic aldehyde is selected from unsubstituted benzaldehyde, benzaldehyde having from one to three substituent groups selected from $C_{1-4}$ alkyl, halogen and $C_{3-5}$ alkylene forming a carbocyclic ring with adjacent carbon atoms on an unsaturated hydrocarbon ring, including p-methyl, p-ethyl, 2,4-dimethyl, 3,4-dimethyl and 2,4,5-trimethyl benzaldehyde, 5-indan aldehyde and 5', 6', 7', 8'-etrahydro-2-naphthaldehyde, or any of the corresponding benzaldehydes to the asymmetric or monoacetal compounds listed above. Of course, in order to produce mostly monoacetal compounds, a molar ratio of alditol to benzaldehyde of about 1:1 is necessary while triacetals require about a 1:3 molar ratio in general.

Mixtures of the aromatic aldehydes may be provided and will result in a distribution of diacetals having the same or different aromatic components, referred to as symmetric and asymmetric diacetals, respectively. The aromatic aldehydes typically react with the polyhydric alcohol to form acetals in the 1:3 and 2:4 positions. Also within the scope of the present invention are triacetals formed by the condensation of three moles of an aromatic aldehyde and one mole of a polyhydric alcohol having six or more hydroxyl groups. The triacetals are typically formed at the 1:3, 2:4 and 5:6 positions of the alcohol.

The polyhydric alcohols have five or more hydroxyl groups. The sugar alcohols represented by the formula $HOCH_2(CHOH)_n CH_2OH$, where n=3–5, have been found to be especially useful. Preferably, the polyhydric alcohol is a pentahydric or hexahydric alcohol, most preferably xylitol or sorbitol. The polyhydric alcohol can be added to the reaction mixture as a solid, molten liquid, or as an aqueous solution.

The reaction medium for this inventive procedure is water, although small amounts of other solvents (such as alcohols, benzene, and the like) may be present as minor impurities. The water may also comprise other constituents such as salts (e.g., chlorides, sulfates, and the like), although it is preferred that the water be deionized prior to utilization within the method. The aqueous nature of this inventive process thus provides a cost-effective process (with such a plentiful, inexpensive, reusable, raw material) which is safe to handle and use, for clear reasons.

The mineral acid is selected from primarily hydroacids, such as, without limitation, hydrochloric acid, sulfuric acid, phosphoric acid, hydrofluoric acid, hydrobromic acid, hydroiodic acid, sulfurous acid, carbonic acid, phosphorous acid, and the like. Such a component is used as the actual catalyst to effectuate the acetalization of the alditol backbone. Although concentrated varieties of such acids are possible, it has also been found that not only is a safer reaction permitted through utilization of less concentrated compositions (for instance, and without limitation, instead of 12M HCl, concentrations of from 5 to 7, more preferably about 6 to 6.5M HCl), but a more effective reaction in terms of yield of acetal alditol product is potentially available as well. This phenomenon is more prevalent which symmetrical DBS compounds are formed, although asymmetrical DBS compounds may also benefit from such a concentration reduction.

As noted above, the catalysis of reactants within the inventive reaction mixture is highly dependent upon the ability of the catalyst to actually contact and thus effectuate catalysis between the components of the mixture itself. Solubility of components within the aqueous acid system is thus of utmost importance; more thorough mixing (and thus greater contact) between catalyst and components permits more effective and higher yields of acetal alditol product. The surfactant component of this inventive reaction is thus of utmost importance as well to effectuating the desired high yield, high purity results. The types of surfactants proper for such a reaction are virtually endless and may be tailored for certain situations, including, without limitation, the solubility of the benzaldehydes within the aqueous acid reaction mixture, environmental considerations, handling issues, cost, availability, compatibility with other components, and the like. Thus, the list of possible surfactants are those which are anionic, cationic, amphoteric, zwitterionic, and nonionic in nature. Compositions of more than one such surfactant may be utilized within the inventive process as well. For this invention, the broad term surfactant is intended to include any long carbon chain (e.g., 6 carbons or greater)-containing compounds with pendant groups such as, without limitation, hydroxyls, alkoxyls, carboxylates and acids, sulfonic acids and sulfonates, quaternary ammoniums, phosphoniums, phosphonic acids and phosphonates, and the like. As anionics, more specific types may be sulfonates, including long-chain substituted-arylsulfonic acids, and the like; cationics include quaternary ammonium salts, phosphonium salts, protonated long chain amines, and the like; nonionics include long-chain substituted phenols, alkoxylated alkanes and alkenes, long-chain alkylarnines, including octadecyl phenol, and the like. The amount of such surfactants added within the inventive reaction and inventive reaction mixture is in relation to the amount added of the benzaldehyde.

The molar ratio between benzaldehyde added and surfactant(s) is from about 1:0.1 to about 1:0.000001; preferably from about 1:0.05 to about 1:0.0001; more preferably from about 1:0.02 to about 1:0.0005; and most preferably between about 1:0.01 and 1:0.0005. In such a situation, the amount added of benzaldehyde is dictated by the type of acetal alditol product desired (mono-, di-, or tri-acetal) in relation to the molar amounts needed of the alditol component. The amount of aqueous acid to be added should be from about 1 to 5 times the amount of the total weight of benzaldehyde and alditol present, with concentrations anywhere between about 2M and 18M depending upon the acid used.

The reaction takes place at room temperature, enerally, although some heating may be followed. Some acids also react exothermically with water (such as sulfuric acid) to generate some internal heat within the system itself All of the components may be mixed together initially, or the surfactant and acid may be first mixed together (under heat, if desired), with subsequent addition of the reactants. The time for reaction may take anywhere from a few minutes (e.g., 10 minutes, as one non-limiting example) to a few days (e.g., 48 hours, as one non-limiting example) depending upon the batch size and the amount of acid catalyst present. Generally, a reaction time of from about 8 hours to about 48 hours, more preferably from about 8 hours to about 36 hours, is sufficient to produce the desired high yield acetal alditol derivatives. Upon production, a solid precipitate is generally formed and neutralized to a pH of from about 6 to about 9.5, with a pH of from about 7.5 to 9, more particularly from about 8.5 to 9, to permit safer handling. Any neutralizer for mineral acids may be utilized such as strong bases like sodium hydroxide, potassium hydroxide, and the like, for this purpose. The washed product can then be dried and collected as a crystalline structure for further utilization in a variety of procedures.

PREFERRED EMBODIMENTS OF THE INVENTION

Examples of the particularly preferred inventive methods are outlined below.

EXAMPLE 1

Preparation of 3,4-Dimethyldibenzylidene Sorbitol With Cationic Surfactant

A one-liter polyethylene beaker equipped with a mechanical stirrer was charged with D-sorbitol (52 g, 0.285 m), 140 g of aqueous sulfuric acid (50% concentrated), 2.0 g of trimethylhexadecyl ammonium chloride, 50% active (0.00313 m), and 53.6 g (0.40 moles) of 3,4-dimethylbenzaldehyde. The mixture was stirred for 16 hours (with stopping due to the formation of an unstirrable powder) and 22 hours of reaction without stirring. A solution of cold water (200 mL) and NaOH (80 g) was then added to neutralize the acidic formulation.

The resultant solids were then filtered, washed in water, and collected for analysis. The resultant mixture was measured as 61 g of 1,3:2,4-bis(3,4-dimethylbenzylidene) sorbitol, for a yield of 73.7% and a purity of about 98.8% (with a small amount of the triacetal formed and some traces of the benzaldehyde remaining).

EXAMPLE 2

Preparation of 3,4-Dimethyldibenzylidene Sorbitol With Nonionic Phenol Surfactant A one-liter polyethylene beaker equipped with a mechanical stirrer was charged with D-sorbitol (52 g, 0.285 m), 140 g of aqueous sulfuric acid (50% concentrated), 1.0 g of octyl phenol (9.5 mole of ethoxylate) (0.00155 m), and 53.6 g (0.40 moles) of 3,4-dimethylbenzaldehyde. A solution of cold water (200 mL) and NaOH (80 g) was then added after 22 hours of further stirring. The resultant solids were then filtered, washed in water, and collected for analysis. The resultant mixture was measured as 59.2 g of 1,3:2,4-bis(3,4-dimethylbenzaldehyde) sorbitol, for a yield of 71.5% and a purity of about 97.1% (with a small amount of the triacetal formed and some traces of the benzaldehyde remaining).

EXAMPLE 3

Preparation of 3,4-Dimethyldibenzylidene Sorbitol With Amine Surfactant

A one-liter polyethylene beaker equipped with a mechanical stirrer was charged with D-sorbitol (52 g, 0.285 m), 2.0 g of dimethyl dodecylamine (0.0094 m), and 53.6 g (0.40 moles) of 3,4-dimethylbenzaldehyde. Aqueous acid was then prepared by mixing 93.3 g of concentrated HCl and 48 g of water. A 5 mL aliquot of the aqueous acid was then added to the reaction mixture which created an emulsion after 5 minutes. The remaining amount was then introduced and the resultant mixture became solid in about 5 hours. Another addition of aqueous acid was then followed (93.3 g HCl and 63.6 g of water) and the resultant mixture was stirred for another 17.5 hours. A solution of cold water (200 mL) and NaOH (80 g) was then added to neutralize the product to a pH of about 9. The resultant solids were then filtered, washed in water, and collected for analysis. The resultant mixture was measured as 58.8 g of 1,3:2,4-bis(3,4-dimethylbenzaldehyde)sorbitol, for a yield of 71.0%.

EXAMPLE 4

Preparation of 3,4-Dimethyldibenzylidene Sorbitol With Anionic Surfactant

A one-liter polyethylene beaker equipped with a mechanical stirrer was charged with D-sorbitol (52 g, 0.285 m), 2.0 g of dinonylnaphthalene sulfonic acid (0.002 m), and 53.6 g (0.40 moles) of 3,4-dimethylbenzaldehyde. After 1.7 hours of mixing, 140 g of aqueous sulfulic acid (50% concentrated) was then added and the reaction was cooled to about 10° C. The reaction mixture was stirred another 18 hours and two further introductions of 140 g of aqueous sulfuric acid (50% concentrated) were made. A solution of cold water (200 mL) and NaOH (180 g) was then added to neutralize the resultant solution to a pH of about 9. The resultant solids were then filtered, washed in water, and collected for analysis. The resultant mixture was measured as 56.2 g of 1,3:2,4-bis(3,4-dimethylbenzaldehyde)sorbitol, for a yield of 67.9% and a purity of about 97.7% (with a small amount of the triacetal formed and some traces of the benzaldehyde remaining).

EXAMPLE 5

Preparation of 3,4-Dimethyldibenzylidene Sorbitol With Anionic Surfactant

A one-liter polyethylene beaker equipped with a mechanical stirrer was charged with D-sorbitol (52 g, 0.285 m), 1.0 g of dodecylbenzene sulfonic acid (0.003 m), and 53.6 g (0.40 moles) of 3,4-dimethylbenzaldehyde. Aqueous acid was then prepared by mixing 86.2 g of concentrated HCl and 53.8 g of water (about 6.2 M). After the initial reactants mixed for about 1 hour, the aqueous acid solution was then added. After 22 hours further hours of mixing, a solution of cold water (200 mL) and NaOH (38.4 g) was then added to neutralize the product to a pH of about 9. The resultant solids were then vacuum filtered, washed in water, and collected for analysis. The resultant mixture was measured as 59.7 g of 1,3:2,4-bis(3,4-dimethylbenzaldehyde)sorbitol, for a yield of 72.1% and a purity of about 100.8% with de minimis amounts of triacetal and benzaldehyde).

EXAMPLE 6

Preparation of 2,4-Mono(4-fluoro-3-methylbenzylidene)sorbitol

A two liter cylindrical shaped reaction flask equipped with a mechanical stirrer was charged with 237.37 g of sorbitol (1.303 mole), 250 mL of water, 22.50g of 4-fluoro-3-methylbenzaldehyde (0.1629 moles), 40 mL of concentrated HCl, and 0.20 g of dodecylbenzene sulfonate. The reaction mixture was then stirred for 14 h at 25° C. After neutralization with 56.0 g of KOH, crude 2,4-Mono(4-fluoro-3-methylbenzylidene)sorbitol was filtered and collected. The crude product was recrystallized from water several times to give 3.31 g of 2,4-mono(4-fluoro-3-methylbenzylidene)sorbitol having the structure of:

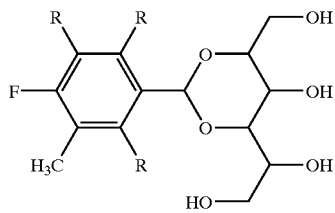

The purity was about 98% as judged by GC. The melting point was measured (DSC @ 20° C./min) to be about 178.0° C.

EXAMPLE 7

Preparation of 2,4-Mono(3-bromo-4-ethylbenzylidene)sorbitol

A 400 mL reaction vessel fitted with a mechanical stirrer was charged with sorbitol (64 g, 0.36 mol), water (20 g), concentrated HCl (45 g) and dodecylbenzenesulfonic acid (0.4 g). After stirring for 10 min, 3-bromo-4-ethylbenzaldehyde (42.6 g, 0.20 mol) was added. The mixture was stirred for 24 hours, then neutralized with aqueous KOH until the pH was 10. The solids were collected by filtration and washed with water and methanol to give 2,4-mono(3-bromo-4-ethylbenzylidene)sorbitol as a white powder (45 g, 59% yield), m.p. 187–189° C. by melting point apparatus.

EXAMPLE 8

Production of 3,4-dichloro/5-indanylidene DBS

A two liter cylindrical shaped reaction flask equipped with a mechanical stirrer was charged with D-sorbitol (25.2 g, 0.138 m), ice (23.6 g), concentrated HCL (44.5 g) and 0.38 g of dodecylbenzene sulfonate. After fifteen minutes of stirring, 24.2 g (0.139 m) of 3,4-dichlorobenzaldehyde and indan aldehyde (96% beta-isomer)(18.5 g, 0.138 m) were added as a mixture. A solution of cold water (200 mL) and KOH (72.0 g) was then added after 48 hours of further stirring. The resultant solids were then filtered, washed in hot water and hot methanol and vacuum-dried. Deionized water (400 mL) was then added to the resultant solution, precipitating a white solid, which was then filtered and washed in methanol to give a mixture of 1,3-O-(3,4-dichlorobenzylidene):2,4-O-(5-indanylidene) sorbitol and 1,3-O-(5-indanylidene):2,4-O-(3,4-dichlorobenzylidene) sorbitol as a tan solid (98% pure). DSC analysis of the solid @ 20° C./min showed multiple melting transitions at 256.1 and 258.8° C.

EXAMPLE 9

Production of 4-nitro/3,4-dimethyl DBS

A two liter cylindrical shaped reaction flask equipped with a mechanical stirrer was charged with 25.4 g of D-sorbitol (0.139 mole), 15.4 g of water, 34.8 g of concentrated HCl, and 0.38 g of dodecylbenzene sulfonate were stirred for about 10 minutes. Subsequently, 20.8 g (0.138 moles) of 4-nitrobenzaldehyde and 18.5 g (0.138 moles) of 3,4-dimethylbenzaldehyde were charged as a mixture and added to the homogenous mixture. A solid block of material formed within one hour of reaction and stirring was impossible. 200 mL of cold water and 56.2 g of KOH were then added permitting filtering of the resultant solids. The yellow filtrate measured a pH of about 14. The remaining solids were then washed with 300 mL of hot water and then 200 mL of hot methanol yielding a tan solid of 4-nitro/3,4-dimethyl asymmetric DBS (46.5 g) mixture. The components of this mixture were determined to be (by Gas Chromatography) 15.1% 3,4-dimethyldibenzylidene sorbitol, 18.9% 4-nitrodibenzylidene sorbitol, and 62.4% mixed asymmetrics of 1,3-O-(4-nitrobenzylidene):2,4-O-(3,4-dimethylbenzylidene)sorbitol and 1,3-O-(3,4-dimethylbenzylidene):2,4-O-(4-nitrobenzylidene)sorbitol. The melting point was measured to be about 223.7–226.9° C. through DSC analysis.

EXAMPLE 10

Production of Asymmetric 4-nitro/3,4-methylenedioxy DBS

A two liter cylindrical shaped reaction flask equipped with a mechanical stirrer was charged with 25.2 g of D-sorbitol (0.138 mole), 34.7 g of concentrated HCl, and 0.5 g of dodecylbenzene sulfonate were stirred for about 10 minutes. Subsequently, 21.0 g (0.139 moles) of 4-nitrobenzaldehyde and 20.9 g (0.139 moles) of piperonal (3,4-methylenedioxybenzaldehyde) were charged as a mixture and added to the homogenous mixture. After two hours the reaction mixture turned yellow and some began to adhere to the sides of the flask. After seven more hours of such mixing, 200 mL of cold water and 56.8 g of KOH were then added and stirred for another 8 hours. Subsequently, the resultant solids were then collected, washed (in boiling water and boiling methanol) and filtered. The yellow-green filtrate measured a pH of about 14. This procedure yielded about 28 g of the 4-nitro/3,4-methylenedioxy asymmetric DBS mixture. The components of this mixture were determined to be (by Gas Chromatography) 9.06% bis(3,4-methylenedioxybenzylidene) sorbitol, 16.63% bis(4-nitrobenzylidene)sorbitol, and 74.31% mixed asymmetries of 1,3-O-(4-nitrobenzylidene):2,4-O-(3,4-methylenedioxybenzylidene)sorbitol and 1,3-O-(3,4-methylenedioxybenzylidene):2,4-O-(4-nitrobenzylidene) sorbitol. The melting point was measured to be about 194.2–204.2° C. through DSC analysis.

EXAMPLE 11

Preparation of 2-Naphthyl/3,4-dimethyl DBS Sorbitol

A one liter reaction flask equipped with a mechanical stirrer was charged with 21.8 g of sorbitol (0.12 mol), 24 g of water, 46 mL of concentrated HCl, and 0.5 g of dodecylbenzene sulfonate. This mixture was stirred for about ten minutes, at which point a solution of 2-naphthaldehyde (15.6 g, 0.1 mole) in 20 mL of water, and 3,4-dimethylbenzaldehyde (13.4 g, 0.1 mole) was added. The mixture was stirred for 4 h. Cold water and KOH were then added to the reaction mixture. The solids were collected by vacuum filtration and washed with water and methanol to give a yellow solid analyzed by gas chromatography to be a mixture of the two asymmetries, 1,3-O-(2-Naphthylidene):2,4-O-(3,4-dimethylbenzylidene)sorbitol and 1,3-O-(3,4-dimethylbenzylidene)-2,4-O-(2-naphthylidene)sorbitol.

EXAMPLE 12

Preparation of Bis(3-bromo-4-methylbenzylidene) sorbitol

To an open reaction vessel equipped with a mechanical stirrer was charged with D-sorbitol (20.1 g, 0.1110 g), concentrated HCl (24.34 g) and 0.27 g of, dodecylbenzene sulfonate. After five minutes of stirring, 43.8 g (0.220 m) of 3-bromo-4-methylbenzaldehyde and 10.72 g of water were added as a mixture. A solution of cold water (1 L, cooled in ice) and KOH (32.3 g) was then added after 48 hours of further stirring. The resultant solids were then filtered, washed in hot water, then hot methanol, then cold toluene, and finally boiling methanol again. Deionized water (400 mL) was then added to the resultant filtrate, precipitating a white solid, which was then filtered and washed in methanol to give 3-bromo-4-methyldibenzylidene sorbitol as a white solid. DSC analysis of the solid @ 20° C./min showed a melting point of 277.4–279.3° C.

EXAMPLE 13

Preparation of Asymmetric 3-Bromo-4-ethyl/3,4-dimethyl DBS

To an open reactor equipped with a mechanical stirrer was charged with 25 g of sorbitol (0.14 mole), concentrated HCl (34.8 g), and 0.38 g of dodecylbenzene sulfonate were charged to an open reaction vessel and stirred. After five minutes, 32 g of ground 2-(3-bromo-4-ethylphenyl)-1,3-dioxane (0.12 mol) and 3,4-dimethylbenzaldehyde (21 g; 0.16 mol) were mixed together with the initial formulation. After 8 hours of stirred reaction, 200 mL of cold water and KOH (72 g) were added. The resultant solids were then filtered and washed in basic water (800 mL with small amounts of KOH), then hot methanol (800 mL), then room temperature toluene (500 mL). Upon the addition of deionized water (400 mL) a white precipitate formed which was then dried by suction filtration and washed by stirring in methanol (800 mL), yielding 3-bromo-4-ethyl/3,4-dimethyl DBS mixtures as a light tan solid. Gas Chromatography analysis of the material indicated that it consisted of a mixture of bis(3-bromo-4-ethylbenzylidene)sorbitol (10.3%), bis(3,4-dimethylbenzylidene)sorbitol (34.8%), and the remainder an asymmetric mixture of 1,3-O-(3-bromo-4-ethylbenzylidene):2,4-O-(3,4-dimethylbenzylidene)sorbitol and 1,3-O-(3,4-dimethylbenzylidene):2,4-O-(3-bromo-4-ethylbenzylidene)sorbitol. A melting transition was observed at 256.7–257.5° C. when heated at 3° C./min on an Electrothermal 9300 Melting Point Apparatus.

EXAMPLE 14

Preparation of Asymmetric 3-Bromo-4-isopropyl/3,4-Dimethyl DBS

To an open reactor equipped with a mechanical stirrer was charged with 20.1 g of sorbitol (0.137 mole), concentrated HCl (34.8 g), and 0.34 g of dodecylbenzene sulfonate were charged to an open reaction vessel and stirred. After five minutes, 33.3 g of ground 2-(3-bromo-4-isopropylphenyl)-1,3-dioxane (0.117 mol) and 3,4-dimethylbenzaldehyde (21.0 g; 0.157 mol) were mixed together with the initial formulation. After 8 hours of stirred reaction, 200 mL of cold water and KOH (72 g) were added. The resultant solids were then filtered and washed in basic water (800 mL with small amounts of KOH), then boiling a methanol (800 mL), yielding an asymmetric mixture of 3-bromo-4-isopropyl/3,4-dimethyl DBS as a light tan solid (6.9 g), exhibiting a melting point of 230.6–236.3°. Gas Chromatography analysis of the material indicated that it consisted of a mixture of bis(3-bromo-4-isopropylbenzylidene)sorbitol (1.8%), bis(3,4-dimethylbenzylidene)sorbitol (65.1%), and the remainder an asymmetric mixture of 1,3-O-(3-bromo-4-isopropylbenzylidene):2,4-O-(3,4-dimethylbenzylidene) sorbitol and 3-bromo-1,3-O-(3,4-dimethylbenzylidene):2,4-O-(3-bromo-4-isopropylbenzylidene)sorbitol.

EXAMPLE 15

Preparation of Asymmetric 3-Bromo-4-methyl/3,4-dimethyl DBS

To an open reactor equipped with a mechanical stirrer was charged with 25 g of sorbitol (0.14 mole), concentrated HCl (34.8 g), and 0.38 g of dodecylbenzene sulfonate were charged to an open reaction vessel and stirred. After five minutes, 30.3 g of ground 2-(3-bromo-4-methylphenyl)-1,3-dioxane (0.117 mol) and 21 g (0.157 mol) of 3,4-dimethylbenzaldehyde were mixed together with the initial formulation. After 8 hours of stirred reaction, 200 mL of cold water and KOH (72 g) were added. The resultant solids were then filtered and washed in basic water (800 mL with small amounts of KOH), then hot methanol (800 mL), then room temperature toluene (500 mL). The resultant solution was then poured into 400 mL of deionized water, thus precipitating a white solid which was then collected, dried by suction filtration, and washed by stirring in methanol (2 L), yielding 3-bromo-4-methyl/3,4-dimethyl DBS as a light tan solid. Gas Chromatography analysis of the material indicated that it consisted of a mixture of bis(3-bromo-4-methylbenzylidene)sorbitol (15.2%), bis(3,4-dimethylbenzylidene)sorbitol (24.5%), and the remainder an asymmetric mixture of 1,3-O-(3-bromo-4-methylbenzylidene):2,4-O-(3,4-dimethylbenzylidene) sorbitol and 1,3-O-(3,4-dimethylbenzlidene):2,4-O-(3-bromo-4-methylbenzylidene)sorbitol. A melting transition was observed at 271.9–274.5° C. when heated at 3° C./min on an Electrothermal 9300 Melting Point Apparatus.

EXAMPLE 16

Preparation of 4-Chloro/3-bromo-4-isopropyl asymmetric DBS

To an open reactor equipped with a mechanical stirrer was charged with 12.6 g of sorbitol (0.0692 mole), concentrated HCl (15 mL), 7.8 g of water, 15.7 g of 3-bromo-4-isopropylbenzylaldehyde (0.0692 mol), 9.69 g of 4-chlorobenzaldehyde (0.069 mol), and 0.2 g of dodecylbenzene sulfonate and the reactants were stirred together for 24 hours. A white solid precipitate formed during the reaction and was neutralized after the reaction was complete with a solution of KOH (10 g) in water (250 mL). The resultant solids were then collected by filtration and washed by stirring in boiling water then boiling cyclohexane to provide a 4-chloro/3-bromo-4-isopropyl asymmetric DBS mixture as a white powder exhibiting a melting point of 212.5–218.9°. Gas Chromatography analysis of the material indicated that it consisted of a mixture of bis(3-bromo-4-isopropylbenzylidene)sorbitol (14%), bis(4-chlorobenzylidene)sorbitol (45%), and the remainder an asymmetric mixture of 1,3-O-(3-bromo-4-isopropylbenzylidene):2,4-O-(4-chlorobenzylidene)sorbitol and 1,3-O-(4-chlorobenzylidene):2,4-O-(3-bromo-4-isopropylbenzylidene)sorbitol.

EXAMPLE 17

Preparation of Bis(5-indanylidene)Sorbitol

A 400 mL reaction vessel fitted with a mechanical stirrer was charged with sorbitol (32 g, 0.18 mol), water (20 g), concentrated HCl (45 g) and dodecylbenzenesulfonic acid (0.4 g). After stirring for 10 min, 5-formylindan (29 g, 0.20 mol) was added. The mixture was stirred for 18 h, then neutralized with aqueous KOH. The solids were collected by filtration and washed with water and methanol to give Indan DBS as a white solid (14 g, 33% yield).

EXAMPLE 18

Preparation of Bis(3,4-diethylbenzylidene)sorbitol

A mixture of sorbitol (2.6 g, 14 mmol), 3,4-diethylbenzaldehyde (4.5 g, 28 mmol), water (2 g), concentrated HCl (4 g) and dodecylbenzene sulfonic acid (0.05 g) was stirred for 12 h. The mixture was then neutralized with aqueous KOH. The solids were collected by filtration and washed with cyclohexane and water to give 1,3:2,4-bis(3,4-diethylbenzylidene) sorbitol as a white solid (95% pure).

EXAMPLE 19

Preparation of Bis(3-ethyl-4-methylbenzylidene) sorbitol

A mixture of sorbitol (7.3 g, 0.04 mol), the propylene glycol cyclic acetal of 3-ethyl-4-methyl benzaldehyde (18 g, 0.08 mol), water (7 g), concentrated HCl (13 g) and dodecylbenzene sulfonic acid (0.14 g) was stirred for 12 h. The mixture was then neutralized with aqueous KOH. The solids were collected by filtration and washed with water to give 1,3:2,4-bis(3-ethyl-4-methylbenzylidene)sorbitol as a white solid (95% pure).

Preparation of Bis(3-ethyl-4-methylbenzylidene) sorbitol

A one liter four-necked cylindrical shaped reaction flask equipped with a mechanical stirrer was charged with D-sorbitol (86.6 g, 0.33 m) and an aqueous acid solution prepared by mixing 118 g of concentrated HCl and 148 g of ice. The reactants mixed well together. Subsequently, 77.7 g (0.58 moles) of 3,4-dimethylbenzaldehyde were then added dropwise to the reaction mixture over a four hour time frame. No visible solid product was noticed after mixing for another few hours.

Preparation of Bis(3-ethyl-4-methylbenzylidene) sorbitol

A one liter four-necked cylindrical shaped reaction flask equipped with a mechanical stirrer was charged with D-sorbitol (2.018 g, x.x m) and 1.801 g (0.xx moles) of 3,4-dinethylbenzaldehyde in the presence of 0.04 g of para-toluenesulfonic acid (PTSA) and a solution of 1.5 g of sulfuric acid in 3.5 g of water. No visible solid product was noticed after mixing for twenty-three hours.

EXAMPLE 22 (COMPARATIVE)

Preparation of Bis(3,4-diethylbenzylidene)sorbitol Through Methanol Process

A one liter four-necked cylindrical shaped reaction flask equipped with a Dean-Stark trap, condenser, thermometer, nitrogen inlet, and a mechanical stirrer was charged with 42.00 g of sorbitol (0.2306 mole), 700 mL of cyclohexane, 3,4-diethylbenzaldehyde (0.2306 moles), 80 mL of methanol, and 2.5 g of water. The reaction was stirred and heated, at which point 3.0 g of p-toluenesulfonic acid was then added. The reaction then proceeded with increased temperature to reflux at which point water was then removed continuously from the trap with solvent added as needed. After further heating, 40 mL of methanol were added to the mixture, which lowered the temperature. After 6 hours, the reaction mixture was cooled and analyzed. No visible product was formed.

EXAMPLE 23 (COMPARATIVE)

Preparation of Bis(3-ethyl-4-methylbenzylidene) sorbitol Through Methanol Process A one liter four-necked cylindrical shaped reaction flask equipped with a Dean-Stark trap, condenser, thermometer, nitrogen inlet, and a mechanical stirrer was charged with 42.00 g of sorbitol (0.2306 mole), 700 mL of cyclohexane, 3-,ethyl-4-methylbenzaldehyde (0.2306 moles), 80 mL of methanol, and 2.5 g of water. The reaction was stirred and heated, at which point 3.0 g of p-toluenesulfonic acid was then added. The reaction then proceeded with increased temperature to reflux at which point water was then removed continuously from the trap with solvent added as needed. After further heating, 40 mL of methanol were added to the mixture, which lowered the temperature. After 6 hours, the reaction mixture was cooled and analyzed. No visible product was formed.

It is thus evident that the versatility of the inventive production method as well as the ability shows the unexpected benefits available from such a procedure.

Having described the invention in detail it is obvious that one skilled in the art will be able to make variations and modifications thereto without departing from the scope of the present invention. Accordingly, the scope of the present invention should be determined only by the claims appended hereto.

That which is claimed is:

1. A method of producing a alditol acetal derivative compound comprising the reaction of at least one substituted benzaldehyde and at least one alditol in the presence of water, at least one mineral acid, and at least one surfactant.

2. The method of claim 1 wherein said alditol acetal derivative is a diacetal compound.

3. The method of claim 1 wherein said alditol is selected from the group consisting of sorbitol, xylitol, and any mixtures thereof, wherein said mineral acid is selected from the group consisting of hydrochloric acid, suliric acid, and any mixtures thereof, and wherein said surfactant is selected from the group consisting of at least anionic surfactant, at least one cationic surfactant, at least one nonionic surfactant, at least one amphoteric surfactant, and any mixtures thereof.

4. The method of claim 3 wherein said surfactant is a sulfonic acid anionic surfactant.

5. The method of claim 3 wherein said surfactant is a quaternary ammonium cationic surfactant.

6. The method of claim 3 wherein said surfactant is an amine surfactant.

7. The method of claim 3 wherein said surfactant is an alkoxylated alcohol nonionic surfactant.

8. The method of claim 2 wherein said alditol is selected from the group consisting of sorbitol, xylitol, and any mixtures thereof, wherein said mineral acid is selected from the group consisting of hydrochloric acid, sulfuric acid, and any mixtures thereof, and wherein said surfactant is selected from the group consisting of at least anionic surfactant, at least one cationic surfactant, at least one nonionic surfactant, at least one amphoteric surfactant, and any mixtures thereof.

9. The method of claim 8 wherein said surfactant is an anionic surfactant having a sulfonic acid moiety.

10. The method of claim 8 wherein said surfactant is a quatemnary ammonium cationic surfactant.

11. The method of claim 8 wherein said surfactant is an amine surfactant.

12. The method of claim 8 wherein said surfactant is an alkoxylated alcohol nonionic surfactant.

13. The method of claim 1 wherein said alditol acetal derivative is a monoacetal compound.

14. The method of claim 13 wherein said alditol is selected from the group consisting of sorbitol, xylitol, and any mixtures thereof, wherein said mineral acid is selected from the group consisting of hydrochloric acid, sulfuric acid, and any mixtures thereof, and wherein said surfactant is selected from the group consisting of at least anionic surfactant, at least one cationic surfactant, at least one nonionic surfactant, at least one amphoteric surfactant, and any mixtures thereof.

15. The method of claim 13 wherein said surfactant is an anionic surfactant having a sulfonic acid moiety.

16. The method of claim 13 wherein said surfactant is a quaternary ammonium cationic surfactant.

17. The method of claim 13 wherein said surfactant is an amine surfactant.

18. The method of claim 13 wherein said surfactant is an alkoxylated alcohol nonionic surfactant.

19. The method of claim 1 where said alditol acetal derivative is an asymmetrical diacetal compound.

20. The method of claim 19 wherein said alditol is selected from the group consisting of sorbitol, xylitol, and any mixtures thereof, wherein said mineral acid is selected from the group consisting of hydrochloric acid, sulfuric acid, and any mixtures thereof, and wherein said surfactant is selected from the group consisting of at least anionic surfactant, at least one cationic surfactant, at least one nonionic surfactant, at least one amphoteric surfactant, and any mixtures thereof.

21. The method of claim 19 wherein said surfactant is an anionic surfactant having a sulfonic acid moiety.

22. The method of claim 19 wherein said surfactant is a quaternary ammonium cationic surfactant.

23. The method of claim 19 wherein said surfactant is an amine surfactant.

24. The method of claim 19 wherein said surfactant is an alkoxylated alcohol nonionic surfactant.

\* \* \* \* \*

UNITED STATES PATENT AND TRADEMARK OFFICE
CERTIFICATE OF CORRECTION

PATENT NO.   : 6,500,964 B2
DATED        : December 31, 2002
INVENTOR(S)  : John G. Lever It is certified that error appears in the above-identified patent and that said Letters Patent is hereby corrected as shown below:

<u>Column 14,</u>
Line 61, delete the word "suliric" and insert the word -- sulfuric --.

<u>Column 15,</u>
Line 18, delete the word "quatemnary" and insert the word -- quaternary --.

Signed and Sealed this

Eleventh Day of March, 2003

JAMES E. ROGAN
*Director of the United States Patent and Trademark Office*